United States Patent
Bonnet et al.

(10) Patent No.: US 7,661,200 B2
(45) Date of Patent: Feb. 16, 2010

(54) METHOD AND DEVICE FOR DETERMINING A PERSON'S MOTIONS

(75) Inventors: Stephane Bonnet, Seyssinet (FR); Regis Guillemaud, La tronche (FR)

(73) Assignee: Commissariat a l'Energie Atomique, Paris (FR)

( * ) Notice: Subject to any disclaimer, the term of this patent is extended or adjusted under 35 U.S.C. 154(b) by 331 days.

(21) Appl. No.: 10/592,799

(22) PCT Filed: Mar. 30, 2005

(86) PCT No.: PCT/FR2005/050201
§ 371 (c)(1),
(2), (4) Date: Sep. 14, 2006

(87) PCT Pub. No.: WO2005/094676
PCT Pub. Date: Oct. 13, 2005

(65) Prior Publication Data
US 2007/0186429 A1    Aug. 16, 2007

(30) Foreign Application Priority Data
Mar. 30, 2004    (FR) .................................. 04 50619

(51) Int. Cl.
*A61B 5/103* (2006.01)
(52) U.S. Cl. ............................. 33/512; 33/1 PT; 33/1 N
(58) Field of Classification Search ................... 33/512, 33/1 PT, 1 N, 281–282, 285
See application file for complete search history.

(56) References Cited

U.S. PATENT DOCUMENTS

| | | | | |
|---|---|---|---|---|
| 4,665,928 A | * | 5/1987 | Linial et al. | 600/595 |
| 5,305,236 A | * | 4/1994 | Germanetti | 701/221 |
| 5,354,317 A | * | 10/1994 | Alt | 607/19 |
| 5,430,435 A | | 7/1995 | Hoch et al. | |
| 5,953,683 A | | 9/1999 | Hansen et al. | |
| 6,050,963 A | | 4/2000 | Johnson et al. | |
| 6,409,687 B1 | | 6/2002 | Foxlin | |
| 6,428,490 B1 | * | 8/2002 | Kramer et al. | 600/595 |
| 6,522,266 B1 | * | 2/2003 | Soehren et al. | 340/988 |
| 6,594,911 B2 | * | 7/2003 | Brunstein et al. | 33/318 |
| 6,734,834 B1 | * | 5/2004 | Baram | 345/8 |
| 7,254,376 B2 | * | 8/2007 | Park et al. | 455/100 |
| 7,269,532 B2 | * | 9/2007 | David et al. | 702/151 |
| 2002/0008630 A1 | * | 1/2002 | Lehrman et al. | 340/669 |
| 2002/0103610 A1 | | 8/2002 | Bachmann et al. | |

FOREIGN PATENT DOCUMENTS

EP    1 460 378    9/2004

* cited by examiner

*Primary Examiner*—G. Bradley Bennett
*Assistant Examiner*—Tania C Courson
(74) *Attorney, Agent, or Firm*—Oblon, Spivak, McClelland, Maier & Neustadt, L.L.P.

(57) ABSTRACT

A sensor worn by a person measures movements of the person. Movements of orientation are not expressed by rotations leading from a stationary reference point to a reference point associated with the sensor, but by angles separating axes or planes of the stationary reference point and axes associated with the wearer, thereby making it possible to better identify his/her movements and his/her activity. The sensor can be applied to the monitoring of patients.

7 Claims, 4 Drawing Sheets

METHOD AND DEVICE FOR DETERMINING A PERSON'S MOTIONS

The subject of this invention is a method and a device for determining movements of a person.

There are numerous uses of such methods for activity monitoring or surveillance purposes. One of them, which is important for the invention, without being limiting, is the surveillance of patients. It is important to provide not only the situation in the space of a person, but also indications concerning his/her posture and even his/her activity or physiological state so as to help to detect a dangerous state and intervene with a lower risk of ineffectiveness.

The surveillance is performed by a sensor associated with the person (who will also be referred to as "the wearer" in this text), often stuck to the chest. It often includes acceleration detectors in which the integration of signals gives to position of the person or physiological indications such as respiration or heartbeat. The movement of the person can be known in position as well as in orientation, according to successive inclinations communicated to the sensor.

French patent 2 838 185 describes a method for determining the orientation of a sensor capable of being placed on a solid body and in particular on a person, estimated by so-called angles of pitch, roll, and yaw, measured from a stationary reference point. The sensor includes magnetometers and accelerometers.

It is then natural to use a stationary reference point comprising an axis directed toward the local magnetic North, an axis directed toward the magnetic East and a third axis directed toward the ground. The method for estimating the orientation of the sensor comprises a mathematical optimisation converging toward the orientation measured. A mobile reference point associated with the sensor is introduced. At each instant, the sensor provides the measurement of the magnetic field and of the gravitational field in the mobile reference point. Then, a rotation giving this measurement is sought, according to the value of the magnetic field expressed in the stationary reference point. This rotation can be expressed in a composition of three basic rotations of Euler angles, such as roll, pitch and yaw angles, so as to obtain the measurements of the sensor. This method is repeated continuously at short time intervals.

The disadvantages of such a method are that it is not easy to interpret the results for deducing the behaviour of the wearer of the sensor. Moreover, the sensor is generally put on by the person who wears it, with uncertainty about the desired orientation, which makes it even more difficult to interpret the results. Finally, the real movements are complex and rapid in the sense that they generally and quickly cause a variation in a plurality of Euler angles of the sensor at one time. The convergence can then become difficult; substantial instabilities are common in practice.

An example of the difficulty of interpreting the movements of the wearer of the sensor can be the following. When the wearer turns around in standing position, about the vertical, the sensor records a variation in the three Euler angles, the variation of the yaw angle, assumed to express this movement of the wearer, being completed by variations in the pitch and roll angles in the general case. In practice, all movements of the wearer, even simple ones, are expressed by combinations of variations, even simple ones, in all of the Euler angles.

Therefore, it has been sought to improve the prior art methods so as to make it easier to work with the indications of the orientation of the person. The invention is based on the observation that the orientation difference of the main axes of the sensor with respect to the natural axes of the wearer are essentially responsible for the difficulties in interpretation of the results, while such differences are, for all practical purposes, inevitable.

The new angles that the sensor will provide will be associated with physical postures of the wearer rather than with orientations of the sensor itself. They will express the person's lateral inclination, his/her longitudinal inclination and the direction toward which the person is turned.

It will thus be easier to determine the type of activity of the wearer.

One aspect of the invention consists of calibrating the position of the sensor even if it was originally positioned improperly: it is necessary simply to take a first measurement when the wearer assumes a conventional posture that he/she is instructed to assume; the original indications given by the sensor correspond to this conventional posture. The orientations of the sensors are continuously recalculated according to these results of the calibration so as to give the orientation of the wearer, the change of which makes it possible to much more easily interpret the movements that he/she is making, with the couplings between the rotation angles being much less significant in the reference point associated with the person.

Other aspects of the invention will now be described in relation to the figures.

Figure 1:
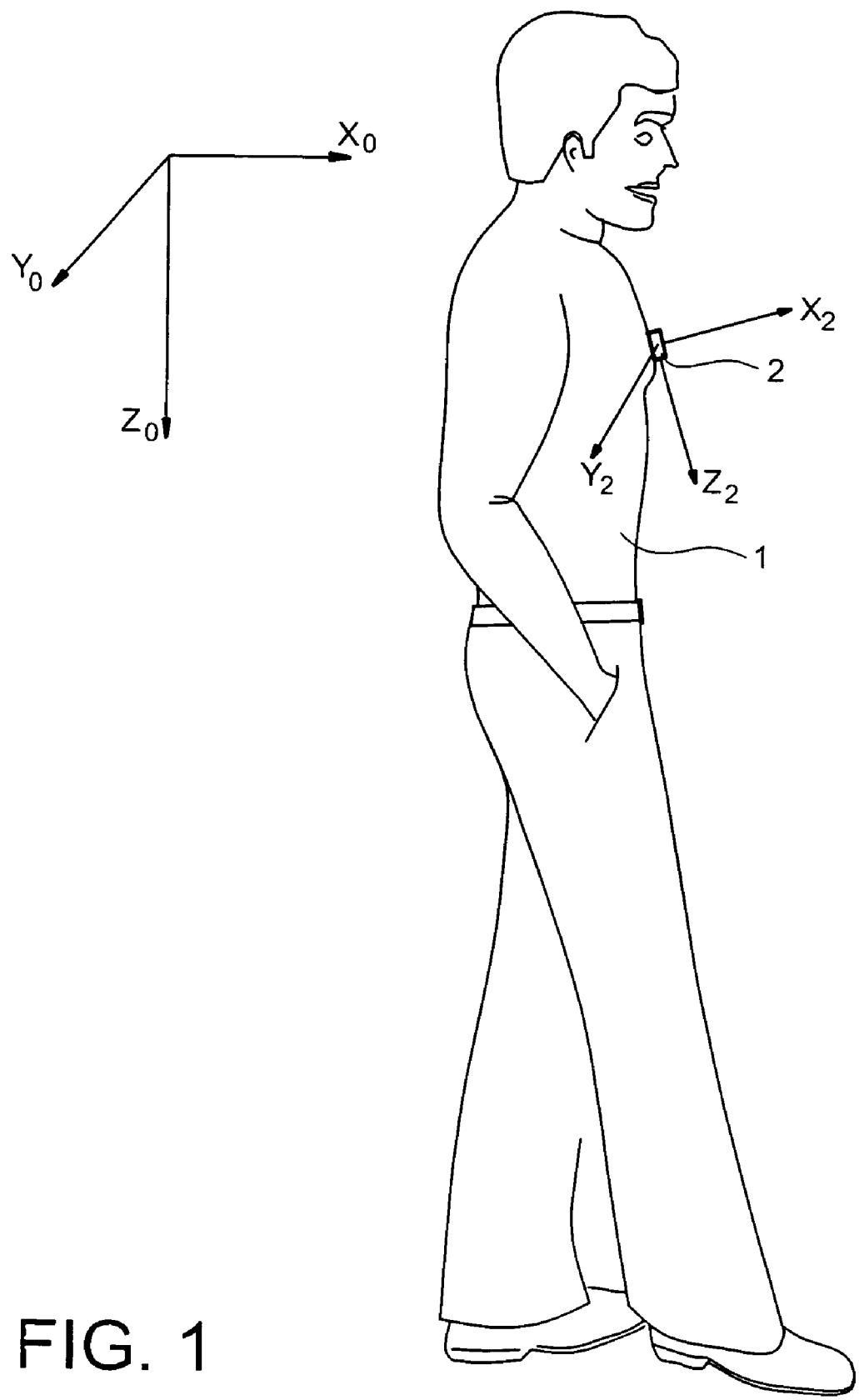
FIG. 1 shows the location of the sensor on the wearer.

FIG. 1 shows that the sensor, designated with the reference 2, is placed on the chest of a wearer 1. It could be placed on the abdomen or in other locations. The sensor 2 is miniature, which enables it to be worn comfortably. The axes $X_0$, $Y_0$ and $Z_0$ define a stationary reference point $R_0$ and are directed toward the magnetic North, the magnetic East and the ground; $X_0$ and $Y_0$ are by definition horizontal and $Z_0$ is vertical. Another reference point $R_2$ is associated with the sensor 2, the axis $X_2$ being directed toward the front of the wearer, axis $Z_2$ toward the feet and axis $Y_2$ toward his/her right-hand side. The known method involves measuring the angles bringing the stationary reference point $R_0$ to the reference point associated with the sensor $R_2$ by a rotation about the axis $Z_0$ with a yaw angle, then by a rotation about the axis $Y_0$ (moved by the yaw rotation) by a pitch angle, then by a rotation about the axis $X_0$ (also moved) by a roll angle.

Figure 2:
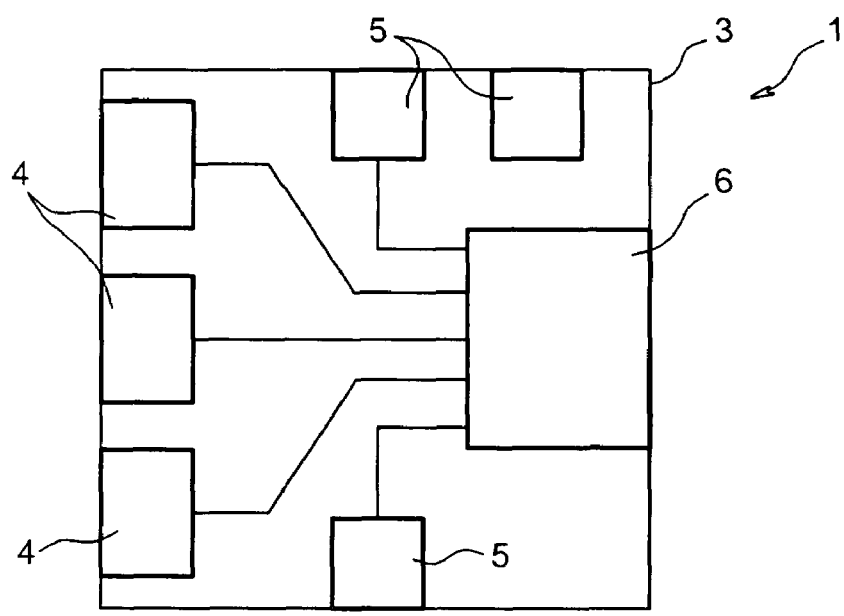
FIG. 2 shows the sensor in its entirety.
Figure 3:
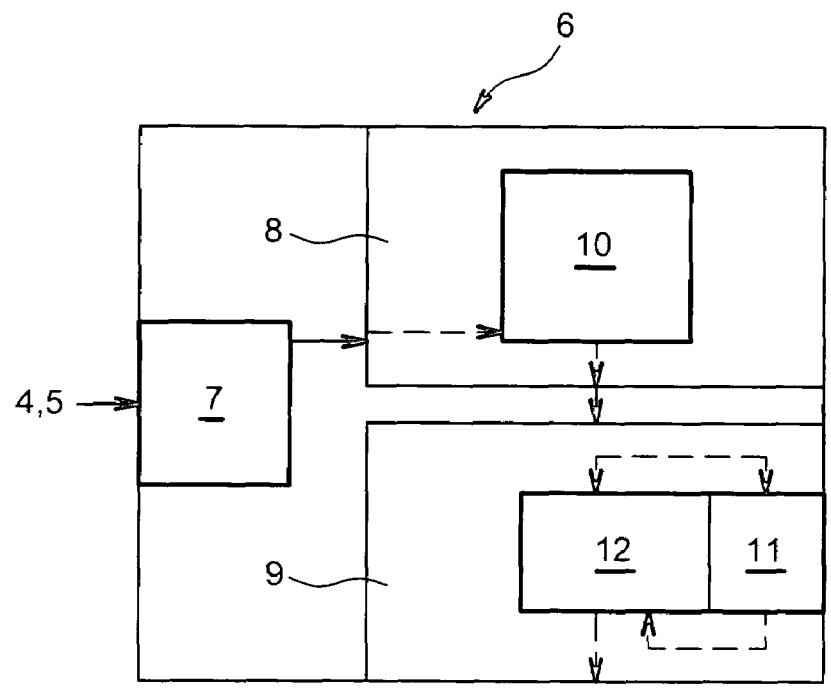
FIG. 3 shows the processing system.

According to FIG. 2, the sensor 2 can comprise a casing 3 containing three accelerometers all designated with the reference 4, three magnetometers all designated with the reference 5 and a processing system 6 to which the accelerometers 4 and magnetometers 5 are connected by wires so as to provide it with their signals. The accelerometers 4 each measure an acceleration component of the movement of the wearer's chest 1 in one of the axes $X_2$, $Y_2$ and $Z_2$ respectively according to the direction of gravity; the magnetometers 5 do the same according to the direction of the Earth's magnetic field. The sensor 2 is held at a constant orientation against the skin or a clothing item of the wearer 1 with adhesive, stitches, a fastening band or any other suitable means. FIG. 3 shows that the signals from the accelerometers 4 or the magnetometers 5 each pass through a standardisation module 7 and are transmitted to a first calculation module 8 that calculates, according to the prior art, the angles of pitch, roll and yaw expressing the rotations between the reference points R0 ($X_0$, $Y_0$ and $Z_0$) and R2 ($X_2$, $Y_2$ and $Z_2$).

We will now discuss the more characteristic aspects of the invention. A second calculation module 9 completes the calculations indicated above in order to express the positions of axes $X_1$, $Y_1$, and $Z_1$ of another reference point $R_1$, associated with the wearer 1, and which appears in FIG. 4. The axis $X_1$ is directed toward the outside of the chest (forward), the axis $Y_1$ is aligned with the shoulders and directed to the right and axis $Z_1$ runs along the trunk and is directed downward. It should be noted that if the sensor 2 is properly positioned, the respective axes of the reference points $R_1$ and $R_2$ are parallel. The invention is fully useful even if this condition is not satisfied.

Figure 4:
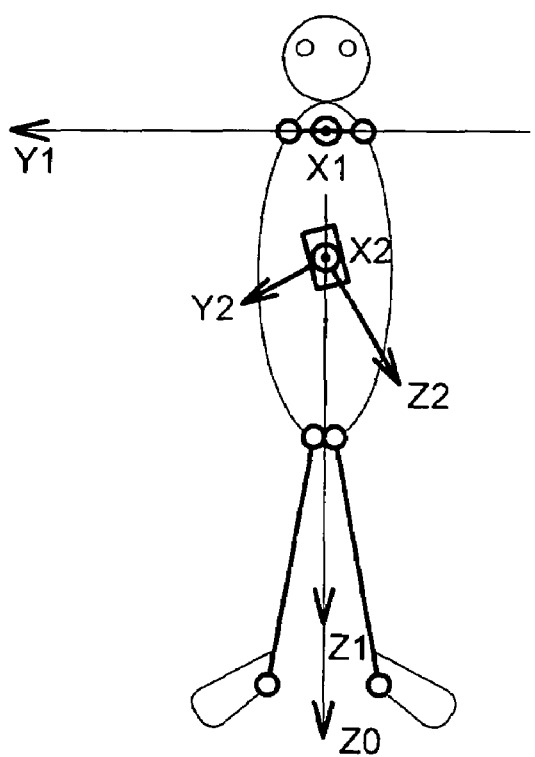
FIGS. 4 and 5 show relationships between two movement points.
Figure 5:
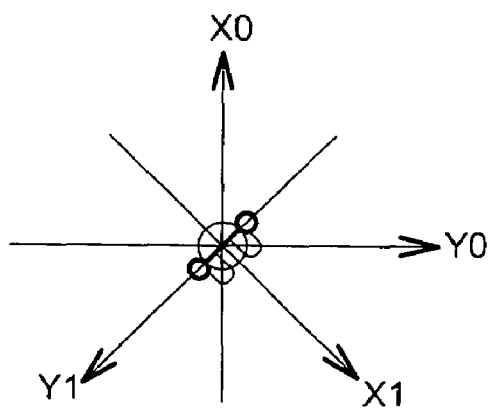

Next, three new angles are defined to characterise the posture of the wearer 1. Their location is shown in FIGS. 4 and 5. The angle $\theta$ is defined between the axis of the vertical and the axis $X_1$ directed forward and expresses the inclination of the wearer 1 at close to 90°; it is close to 0 in the straight position, +90° along the abdomen and −90° along the back.

The lateral angle of inclination or twist angle $\psi$ is defined as the angle between the lateral axis $Y_1$ and the horizontal at close to 90°; it is equal to 90° if the wearer is standing straight or if, for example, he/she is leaning forward, less than 90° if the person leans toward the right and greater than 90° if he/she leans toward the left. Its value may range between 0° and 180°. This angle can indicate whether the person is on his/her right side, left side, back or front when lying down.

The third angle of orientation of the person expresses the direction toward which he/she is turned. It is an angle of azimuth $\phi$ made by the projection of the axis $X_1$ directed forward in the horizontal plane and the axis $X_0$ pointing to the magnetic North.

Figure 6:
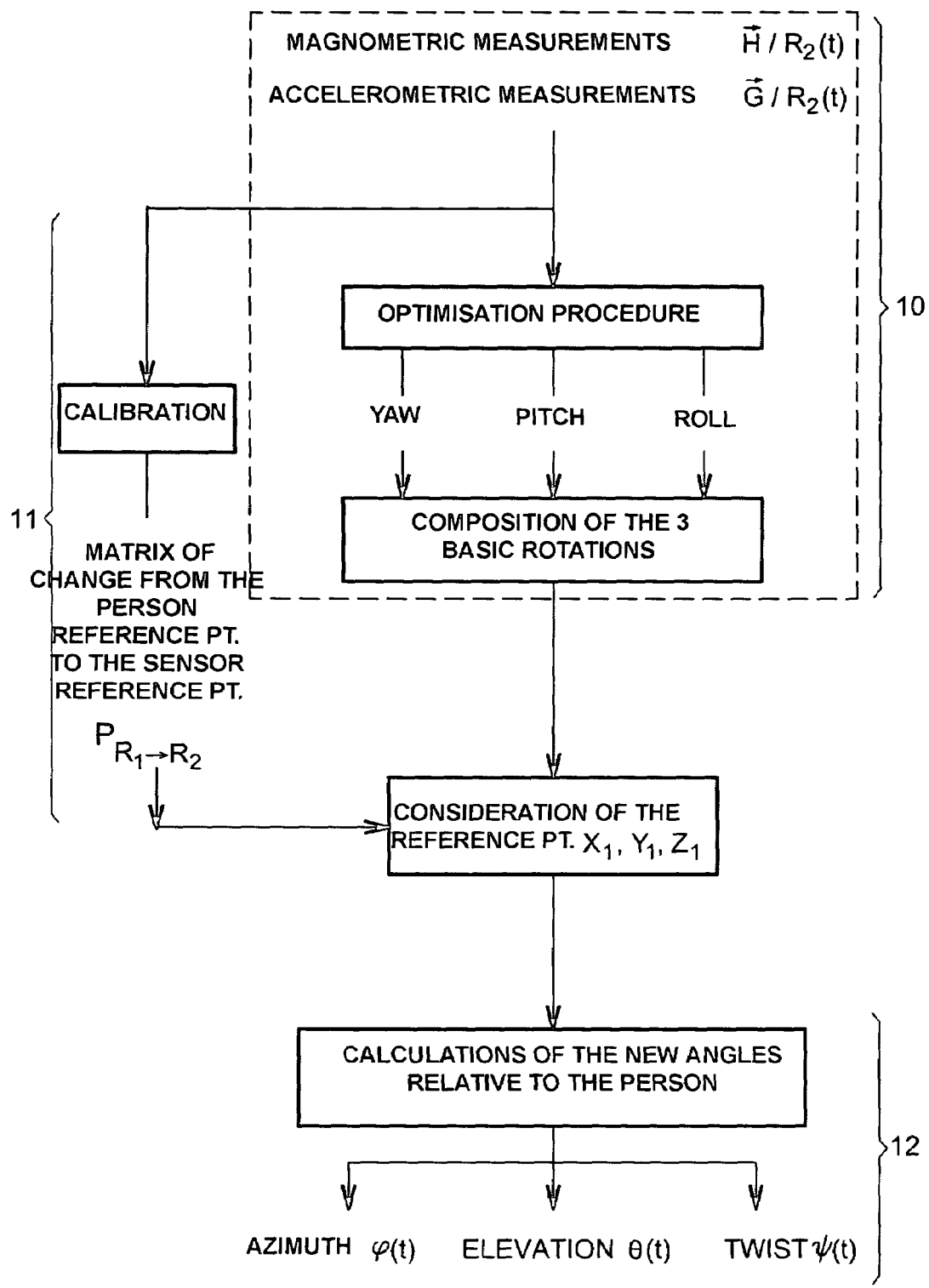
FIG. 6 shows an organisation chart.

The organisation chart of FIG. 6 shows the calculations performed in the processing system 6 in accordance with the invention. The first calculation module 8 gives the normal angles of orientation of the sensor 2 with respect to the stationary reference point using a processor 10 that combines the measurements of the magnetometers and the accelerometers together. These calculations are regularly re-performed in order to monitor the movements of the wearer. In a more original manner, the results are transmitted to the second calculation module 9, which contains a second processor 12 and a calibration memory 11. This second calculation module 9 makes it possible to go from the reference point associated with the sensor $R_2$ to the reference point associated with the wearer $R_1$ and makes an estimation of the angles separating these reference points, which is particularly important if the sensor is attached to the person with its main axes very different from the main axes of the person. It is assumed that the wearer attaches the sensor 2 to his/her chest and that the sensor 2 no longer moves then, so that the reference points $R_1$ and $R_2$ are in a relative invariable position. The person 1 is asked to stand up straight, against a wall for example, for one or two seconds, or possibly lying on the ground in a known direction. The orientation of the reference point associated with the person $R_1$ with respect to the stationary reference point $R_0$ is then precisely known, and preliminary measurements performed with the sensor 2 give the orientation of the reference point associated with the sensor $R_2$ ($X_2$, $Y_2$, $Z_2$) in the stationary reference point $R_0$ ($X_0$, $Y_0$, $Z_0$). It is then easy to deduce the orientation of the reference point associated with the person $R_1$ ($X_1$, $Y_1$, $Z_1$) with respect to the reference point associated with the sensor $R_2$ since the mutual positions of the stationary reference point $R_0$ and the reference point associated with the person $R_1$ are known. This difference in orientation (which can be expressed in the form of three angles) of rotation applied successively, as between $R_0$ and $R_1$ as described above is used as a corrective action for all subsequent measurements. It is stored in the calibration memory 11 after having been registered there during the calibration.

The equation making it possible to go from the reference point associated with the sensor $R_2$ to the reference point associated with the person $R_1$ is therefore $P_{R_2 \to R_1} = P_{R_2 \to R_0}$ ref$\cdot P_{R_0 \to R_2}$ ref, in which P are rotation matrices, $P_{R_2 \to R_0}$ ref expresses the measured orientation of the sensor in the reference state during calibration, and $P_{R_0 \to R_1}$ ref expresses the known orientation of the person in the stationary reference point during calibration.

At any subsequent time t, the second processor 12 applies the equation:

$$P_{R_0 \to R_1}(t) = P_{R_0 \to R_2}(t) \cdot P_{R_2 \to R_1}$$

The results are then transmitted to a monitoring station outside the sensor and not shown.

Another way to calibrate the device would consist of using a second orientation sensor, equivalent to the previous one but used to give orientations in the stationary reference point $R_0$. The second orientation sensor is associated with a part such as a straight edge, preferably with a main axis of measurement in the direction of the straight edge. While the wearer 1 is in a stable posture, seated for example, the straight edge is placed on certain chosen parts of the body so as to deduce the position of the anatomical axes of the reference point associated with the person $R_1$ at this time in the stationary reference point $R_0$. These parts where the straight edge is placed can be the apex of the vertebral column (with the straight edge in a vertical position) and the axis of the shoulders (with the straight edge in a horizontal position). The orientation of the sensor 2 with respect to the person 1 wearing it can be deduced if the measurements of the sensor 2 at this time and the comparison thereof with those of the other sensor are known. This calibration method can give better results than the previous one.

The invention can be used with all types of known sensors, including various combinations of magnetometers, accelerometers, gyrometers or other means; it can complement methods in which the orientation of the sensor is represented by quaternions known to a person skilled in the art rather than by Euler angles.

Clinical trials have shown that the method according to the invention makes it possible to conveniently interpret routine movements of patients and changes in posture between standing, sitting and lying positions.

A remarkable application of the method will probably be the balance analysis: trials have shown that it provided sensitive results under stable and under disturbed conditions, resulting from posture or external elements, and that it therefore made it possible to recognise or even distinguish some of these disturbances. Moreover, the movements for restoring balance can be measured precisely and analysed.

The invention claimed is:

1. A method for determining movement of a person, comprising:
preliminarily calibrating a sensor that is installed on the person by recording a preliminary orientation of the sensor while the person is at a predetermined orientation with respect to a stationary reference;
performing a repeated computation of an orientation of the sensor with respect to the stationary reference, expressed as a combination of rotations from the stationary reference, from signals of the sensor; and
correcting the combination of rotations so as to express rotations of the sensor bound to the person, which includes a vertical axis, a front-back horizontal axis and a left-right horizontal axis, as another combination of rotations of the person that include a side inclination of the person, a front-back inclination of the person and an azimuth rotation of the person.

2. The method according to claim 1, wherein the sensor includes accelerometers and magnetometers.

3. The method according to claim 1, wherein the sensor includes gyrometers.

4. The method according to claim 1, wherein angles of orientation of the sensor are Euler angles.

5. The method according to claim 1, wherein angles of orientation of the sensor are expressed by quaternions.

6. The method according to claim 1, wherein
the preliminary calibrating includes storing an orientation of the person with respect to the stationary reference point and storing an orientation of the sensor with respect to the stationary reference point while the person is at the predetermined orientation, and
the correcting includes converting the combination of rotations of the sensor into the another combination of rotations of the person that include the side inclination of the person, the front-back inclination of the person and the azimuth of the person based the orientation of the person with respect to the stationary reference point and the orientation of the sensor with respect to the stationary reference point.

7. A device configured to determine a movement of a person, comprising:
a memory; and
a processing apparatus configured to
preliminarily calibrate a sensor that is installed on the person by causing a preliminary orientation of the sensor while the person is at a predetermined orientation with respect to a stationary reference to be recorded in the memory,
perform a repeated computation of an orientation of the sensor with respect to the stationary reference, expressed as a combination of rotations from the stationary reference, from signals of the sensor, and
correct the combination of rotations so as to express rotations of the sensor bound to the person, which includes a vertical axis, a front-back horizontal axis and a left-right horizontal axis, as another combination of rotations that include a side inclination of the person, a front-back inclination of the person and an azimuth rotation of the person.

* * * * *